United States Patent
Mark et al.

(10) Patent No.: US 10,357,280 B2
(45) Date of Patent: Jul. 23, 2019

(54) NAVIGATING INTRODUCER FOR TISSUE ACCESS SYSTEM

(71) Applicant: NICO CORPORATION, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 162 days.

(21) Appl. No.: 15/141,426

(22) Filed: Apr. 28, 2016

(65) Prior Publication Data

US 2016/0317182 A1    Nov. 3, 2016

Related U.S. Application Data

(60) Provisional application No. 62/155,099, filed on Apr. 30, 2015.

(51) Int. Cl.
*A61B 17/34* (2006.01)
*A61B 90/00* (2016.01)

(52) U.S. Cl.
CPC ...... *A61B 17/3403* (2013.01); *A61B 17/3421* (2013.01); *A61B 17/3496* (2013.01);
(Continued)

(58) Field of Classification Search
CPC ............ A61B 17/3403; A61B 17/3421; A61B 17/3496; A61B 2090/3983; A61B 2017/347; A61B 2017/3454
See application file for complete search history.

(56) References Cited

U.S. PATENT DOCUMENTS 3,690,323 A    9/1972  Wortman et al.
3,941,127 A *  3/1976  Froning ............ A61B 17/3401
                                                 378/162
(Continued)

FOREIGN PATENT DOCUMENTS

RU    2009124446 A1    1/2011
WO    2007002251 A2    1/2007
WO    2008066543 A1    6/2008

OTHER PUBLICATIONS

A. Shupak, Poplar Science, Feb. 2011, "A Healthy Glow Florescent imaging helps surgeons cut more cancer cells."
(Continued)

*Primary Examiner* — Lauren P Farrar
(74) *Attorney, Agent, or Firm* — Kristin L. Murphy; Honigman LLP

(57) ABSTRACT

A surgical access system is disclosed that includes an outer sheath, an introducer, and a navigational stylet. The outer sheath is defined by an open distal end and an open proximal end and includes a hollow body portion therebetween. The obturator is defined by a distal end and a proximal end. The distal end further comprises a tapered distal tip member that terminates in a distal tip. The navigational stylet is configured to be selectively fixed to the obturator and is configured to indicate the location of the obturator within a patient during use. The obturator is configured to be received within the outer sheath such that the tapered distal tip member protrudes from the open distal end of the outer sheath when the obturator is in an introducing configuration.

8 Claims, 5 Drawing Sheets

(52) U.S. Cl.
CPC . *A61B 2017/347* (2013.01); *A61B 2017/3454* (2013.01); *A61B 2090/3983* (2016.02)

(56) References Cited

U.S. PATENT DOCUMENTS

| | | | |
|---|---|---|---|
| 4,386,602 | A | 6/1983 | Sheldon et al. |
| 4,638,798 | A | 1/1987 | Sheldon et al. |
| 4,798,591 | A | 1/1989 | Okada |
| 5,183,464 | A | 2/1993 | Dubrul et al. |
| 5,320,611 | A | 6/1994 | Bonutti et al. |
| 5,431,676 | A | 7/1995 | Dubrul et al. |
| 5,807,324 | A * | 9/1998 | Griffin, III ......... A61B 18/1492 604/264 |
| 5,860,996 | A | 1/1999 | Urban et al. |
| 6,047,218 | A | 4/2000 | Whayne et al. |
| 6,129,685 | A | 10/2000 | Howard, III |
| 6,179,826 | B1 | 1/2001 | Aebischer et al. |
| 6,226,548 | B1 | 5/2001 | Foley et al. |
| 6,245,052 | B1 | 6/2001 | Orth et al. |
| 6,280,399 | B1 | 8/2001 | Rossin et al. |
| 6,293,952 | B1 | 9/2001 | Brosens et al. |
| 6,331,180 | B1 | 12/2001 | Cosman et al. |
| 6,374,135 | B1 | 4/2002 | Bucholz |
| 6,416,520 | B1 | 7/2002 | Kynast et al. |
| 6,669,685 | B1 | 12/2003 | Rizoiu et al. |
| 6,942,634 | B2 | 9/2005 | Odland |
| 9,307,969 | B2 | 4/2016 | Novak et al. |
| 2003/0045834 | A1 | 3/2003 | Wing |
| 2003/0073934 | A1 | 4/2003 | Putz |
| 2004/0024291 | A1 | 2/2004 | Zinkel |
| 2004/0059375 | A1 | 3/2004 | Ginn et al. |
| 2004/0068172 | A1 | 4/2004 | Nowinski et al. |
| 2004/0102804 | A1 | 5/2004 | Chin |
| 2004/0186346 | A1 | 9/2004 | Smith et al. |
| 2004/0215143 | A1 | 10/2004 | Brady et al. |
| 2007/0270898 | A1 | 11/2007 | Lillehei |
| 2008/0139928 | A1 | 6/2008 | Lubock |
| 2009/0048622 | A1 * | 2/2009 | Wilson ............... A61B 17/3431 606/190 |
| 2009/0312611 | A1 | 12/2009 | Mangiardi |
| 2010/0010315 | A1 | 1/2010 | Mangiardi |
| 2010/0228084 | A1 | 9/2010 | Sato |
| 2011/0190712 | A1 * | 8/2011 | Ciavarella ............ A61B 5/0422 604/265 |

OTHER PUBLICATIONS

Richter, Modern Medicine, Jan. 31, 2011, "New Device May Help Surgeons Resect Brain Tumors," "Fluorescence spectroscopy helps neurosurgeons identify hard-to-see tumor tissue."

Nader Sanal, MD, et al., Jun. 2011, "Intraoperative Confocal Microscopy for Brain Tumors: A Feasibility Analysis in Humans," www.neurosurgery-online.com.

Juan C. Fernandez-Miranda, M.D., et al., J. Neurosurg, vol. 113, Nov. 2010, "High-definition fiber tracking guidance for intraparenchmyal endoscopic port surgery."

Manuel Dujovny, et al., Neurological Research, vol. 37, No. 7, (2010), "Brain Retractor Systems."

T. Nakano et al., Dept. of Neurosurgery, Hirosaki University Graduate School of Medicine (2009), "Endoscopic Treatment of Deep-seated or Multiple Intraparenchymal Tumors: Technical Note."

Amin B. Kassam, et al., J. Neurosurg, vol. 110, Jan. 2009, "Completely endoscopic resection of intrapharenchymal brain tumors."

K. Ogura, et al., Acta Neurochir (Wien, 2006), "Neurosurgical Technique, New microsurgical technique for intraparenchymal lesions of the brain: transcylinder approach."

Chun-Chung Chen, M.D., et al., Journal of Clinical Neuroscience (2005), "A stainless steel sheath for endoscopic surgery and its appliction in surgical evacuation of putaminal haemorrhage."

O'Barlas, et al., Clinical Article, Acta Neurochir (Wien, 2004), "Stereotactically guided microsurgical removal of colloid cysts."

Tetsuhiro Nishihara, M.D., et al., J. Neursurg, vol. 92, Jun. 2000, "A transparent sheath for endoscopic surgery and its application in surgical evauultion of spontaneous intracerebral hematomas."

Donald M. O'Rourke, M.D., et al, "Vycor Medical, Inc.—Business Summary", www.vycormedical.com.

PCT International Search Report dated Jun. 20, 2006 for PCT/US05/39185.

Wedeen, Van J., et al., Science 335, 1628 (2012), "The Geometric Structure of the Brain Fiber Pathways."

\* cited by examiner

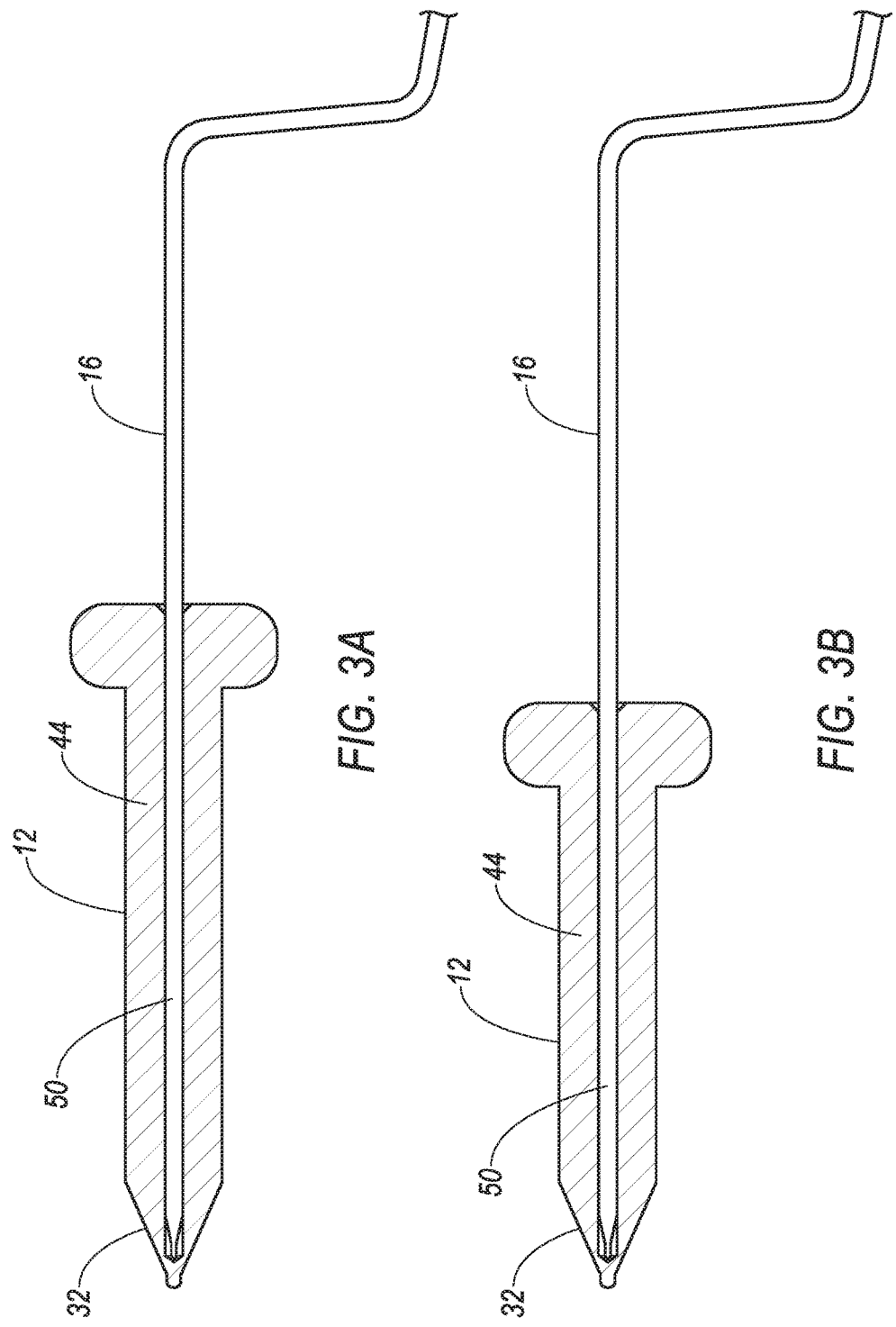

NAVIGATING INTRODUCER FOR TISSUE ACCESS SYSTEM

TECHNICAL FIELD

The present disclosure relates to a tissue access system that cooperates with a navigation system.

BACKGROUND

Diagnosis and treatment of conditions affecting the brain are among the most difficult and complex problems that face the medical profession. The brain is a complex and delicate soft multi-component tissue structure that receives multiple inputs, processes these inputs, responds to the inputs and controls bodily functions through a complex neural network connected to the rest of the body through the spinal cord. The brain and spinal cord are contained within and protected by significant bony structures, e.g., the skull and the spine. Given the difficulty of safely accessing the areas of the brain housed within the hard bony protective skull, as well as navigating the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB), metastases (mets) and functional diseases manifest themselves in the intraparenchymal subcortical space (i.e., the white matter) of the brain are particularly challenging to access, let alone treat. The white matter and the cortex contain eloquent communication structures (neural network) which are located in the subcortical space, called fiber tracts and fascicles which make up the fascicular anatomy. Thus, traditionally, unless the ICH, GB, and/or mets were considered anything but "superficial," such conditions have been considered challenging to access or inoperable, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain and the eloquent real estate that must be traversed to access them.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), sequences such as Diffusion Tensor Imaging (DTI) and Diffusion Weighted Images (DWI). Navigation systems (instrument position tracking systems) have also been improved to allow for the input of many of these improved imaging sequences such as CT and MRI to allow for improved accuracy when tracking instruments within the human body with the information downloaded to the navigational system from these imaging system sequences. These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including the fascicular anatomy. If an abnormality is identified through the use of one or more imaging modalities and/or techniques, it may be necessary or desirable to biopsy or remove the abnormality. The navigational system allows for the intraoperative translation of these sequences during a procedure so that the user may maintain their intraoperative location and orientation during the case.

Once a course of action has been determined based upon one or more imaging techniques, a surgical treatment may be necessary or desired. In order to operate surgically on the brain, access must be obtained through the skull and eleoquent brain tissue containing blood vessels and nerves that can be adversely affected by even slight disturbances. Therefore, great care must be taken when traversing the internal corridor and operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted or removed to obtain access to deliver optics, light and instrumentation. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such tissue disruptive invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary, such as skull base tumors.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument on or within the skull.

While minimally invasive and non-disruptive access systems have been developed now to provide access to previously difficult to access or what were previously considered inoperable areas in the brain and spine, many such access systems do not have the capability to provide navigational information during positioning of the access system.

Notwithstanding the foregoing advances in navigation technology of both frame and frameless stereotactic image guidance techniques, there remains a need for improved instrumentation of these navigational systems which allows for the use with new advances in minimally invasive access systems.

BRIEF DESCRIPTION OF THE DRAWINGS

Exemplary embodiments of the present disclosure will now be described in greater detail with reference to the attached figures, in which:

FIG. 3A is a cross-sectional view of a navigational stylet positioned within a first exemplary introducer element of a surgical access system;

FIG. 3B is a cross-sectional view of a navigational stylet positioned within a second exemplary introducer element of a surgical access systems;

DETAILED DESCRIPTION

Figure 1:
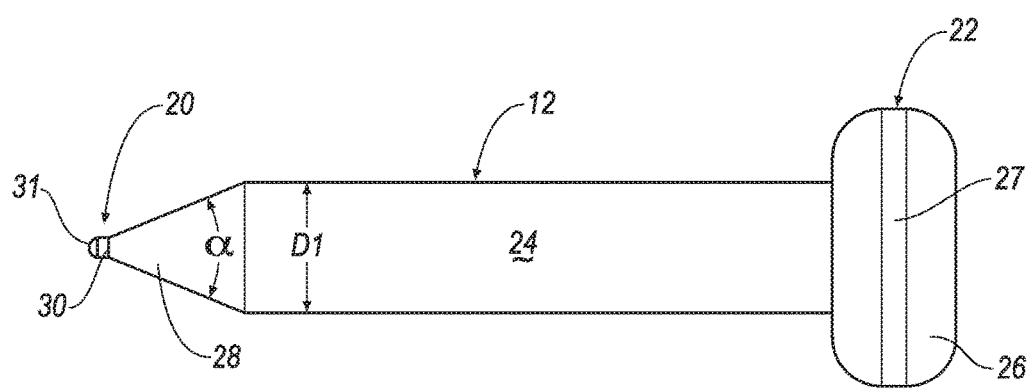
FIG. 1 is an exemplary introducer element of a surgical access system.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens. The surgical access assembly disclosed herein may include components similar to those shown in copending U.S. application Ser. No. 13/444,732, the contents of which are incorporated by reference in its entirety.

Figure 2A:
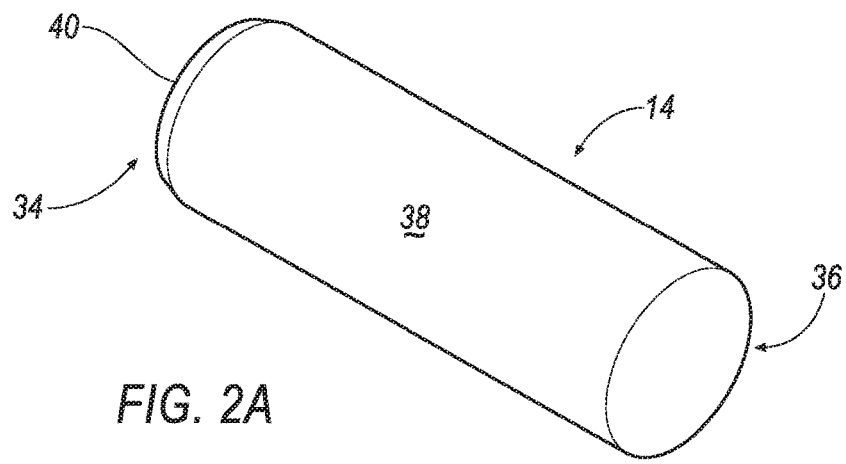
FIG. 2A is a perspective view of an outer sheath of a surgical access system.
Figure 2B:
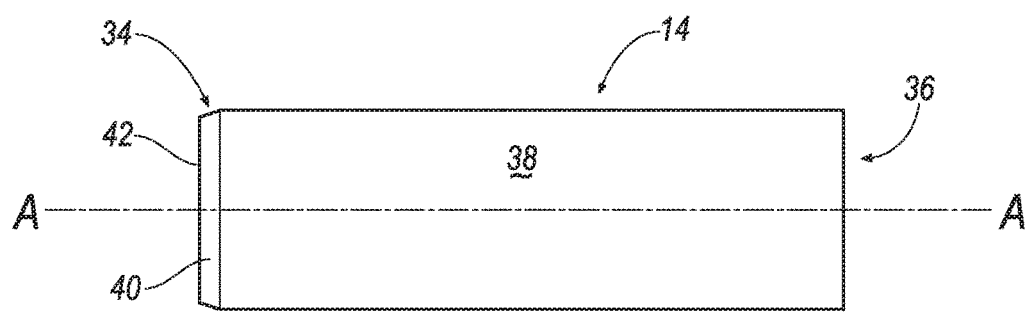
FIG. 2B is a side elevational view of the outer sheath of FIG. 2A.
Figure 2C:
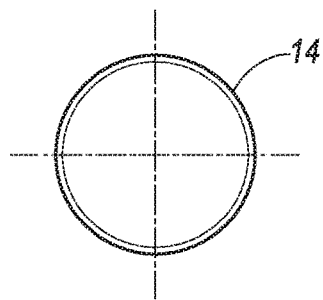
FIG. 2C is an end view of the outer sheath of FIG. 2A.

Generally, a surgical access system 10 (best seen in FIG. 4) of the present disclosure may comprise an introducer 12 (FIG. 1) and an outer sheath 14 (FIGS. 2A-2C). The introducer 12 is configured with a length that is longer than a length of outer sheath 12 such that a distal end of the introducer 12 protrudes a predetermined distance from a distal end of the outer sheath 14, as will be discussed below in greater detail. A stylet with a navigational element 16 may also be used with the surgical access system 10. A locking member 18 may also be provided to selectively lock the stylet 16 to the introducer 16, as will be explained in further detail below.

Turning to FIG. 1, an exemplary arrangement of an introducer 12 is illustrated. Introducer 12 is defined by distal end 20, a proximal end 22, and a body portion 24. A handle portion 26 may be fixedly secured to the proximal end 22. The handle portion 26 may include a textured gripping element 27 to assist in gripping the introducer 12. The body portion 24 is generally solid, with a narrow channel 50 disposed therein.

Distal end 20 is configured with a generally conical shaped distal tip portion 28 that tapers from the body portion 24 toward the distal end 20. In one exemplary arrangement, a distal end 32 of the navigational stylet 16 extends through a distal opening 30 of the introducer 12. With this configuration, the conical shaped distal tip portion 28 cooperates with a non-blunt or non-sharpened distal end 32 of the navigational stylet 16 to provide dilation of tissue, as the surgical access system 10 is directed through brain tissue.

In an alternative exemplary arrangement, distal tip portion 28 tapers toward a closed tip member 31 (as best seen in FIGS. 3A and 3B) so as to prevent coring of tissue as introducer is inserted into the brain. In this arrangement, the distal end 32 of the navigational stylet 16 is offset from the distal tip 28' by a predetermined distance, as will be explained in further detail below.

There are a number of variables that play the selection of the angle α that defines the taper of tip portion 28. These variables include the size of an outer diameter D1 of the introducer 12, the desired length that distal tip portion 28 extends from the body portion 24, and the desired offset for a distal end 32 of the navigational stylet 16 and tip member 28. More specifically, it is contemplated that surgical access assembly 10 will be provided as part of a kit that may include multiple sized outer sheaths 14 and introducers 12, to provide the surgeon with a choice of different diameter sizes and lengths so as to provide flexibility for accessing areas of interest within the brain. However, to insure that the distal tip 31 is determinable regardless of which size diameter D1 of introducer 12 is used, taper angle α may be selectively adjusted. For embodiments that utilize navigation stylet 16 that seats a distal end thereof at a set position within the introducer 12, to maintain an identical offset length between the distal end 32 of navigation stylet 16 and distal tip 31 in different diameter D1 sized introducers 12, taper angle α will need to be increased, as diameter D1 increases.

Figure 5:
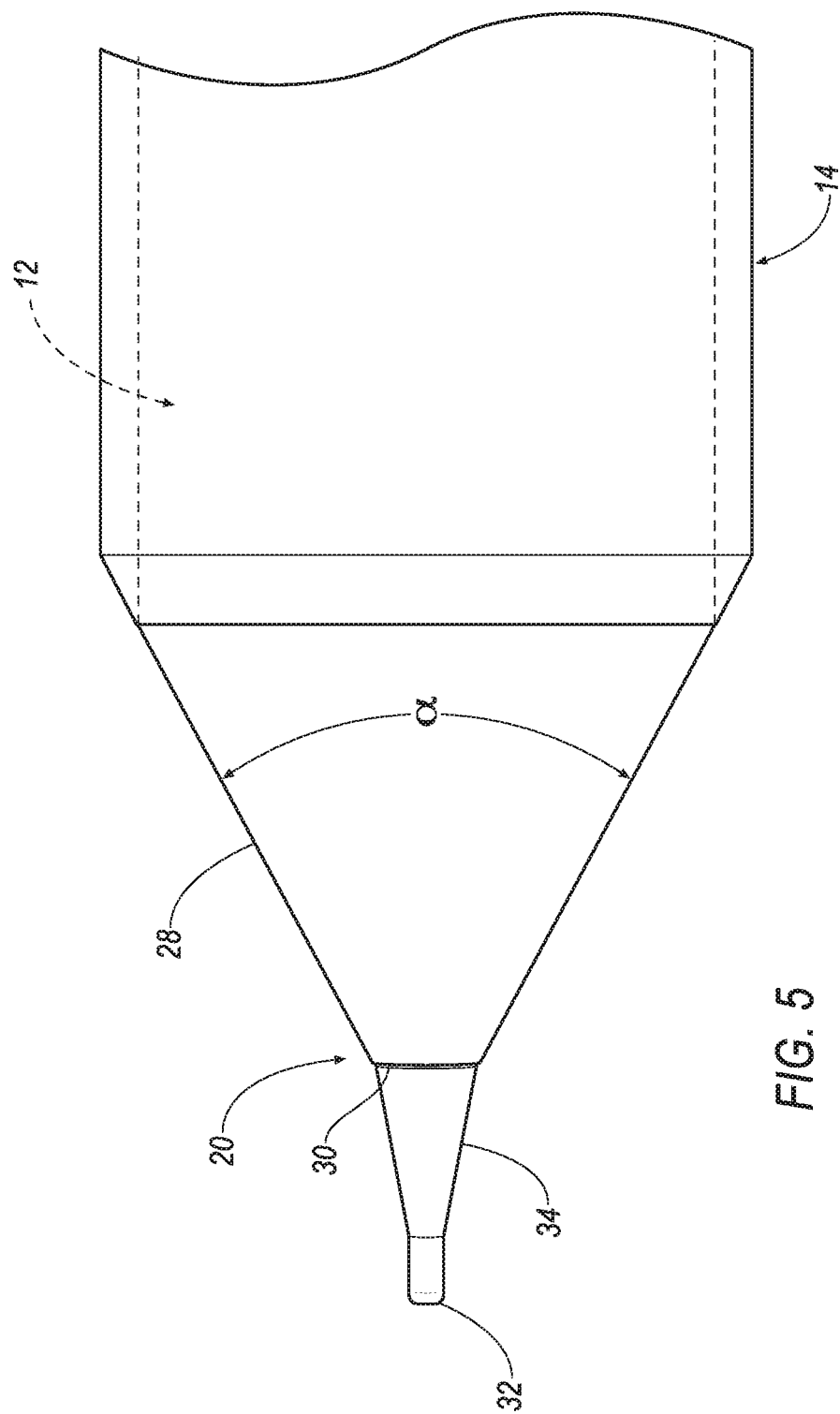
FIG. 5 is an enlarged view of a distal end of the surgical access system taken from area 5 in FIG. 4.

The distal tip 31 is configured to be radiused such that tip member 31 is rounded, and neither blunt, nor sharp. More specifically, tip member 31 is configured so as not to have any flat portions which during insertion can stretch or even tear the delicate tissues such as the vessels, fiber tracts and fascicles found in the brain. Further, because tip member 31 is closed, damage of such delicate tissues and fascicles are also avoided. In the arrangement where the navigational stylet 16 extends through the distal opening 30, the distal end 32 of the navigational stylet 16 may also be configured so as not to have any flat portions. Further, the distal end 32 of the navigational stylet 16 may also have a tapered section 34 that mates with the tapered tip member 28 to provide a smooth transition between the introducer 12 and the navigational stylet 16, as shown in FIG. 5. The configuration of tip member 28 is designed to gently displace and move the tissue into which it is inserted; i.e., atraumatically dilate the tissue to allow for introduction in to an intra-fascicular and para-fascicular manner, as opposed to cutting tissue as surgical access assembly 10 is inserted into the tissue.

Referring to FIGS. 2A-2C, an exemplary embodiment of the outer sheath 14 is shown. The outer sheath 14 is defined by distal end 34 and a proximal end 36 and includes a generally hollow body portion 38. While not shown, outer sheath 14 may also be configured with a grip portion, such as that shown in co-pending U.S. application Ser. No. 13/444,732. In one exemplary arrangement, body portion 38 is constructed of a clear biocompatible material that permits viewing of normal tissue, abnormal tissue, as well as critical structures that are disposed outside of body portion 38 when outer sheath 12 is disposed within such tissue. In one exemplary arrangement, outer sheath 12 is constructed of polycarbonate, though other biocompatible materials may be employed, including resins. Further, the body portion 38 may also be constructed of a non-reflective material so as to reduce eye-fatigue for the surgeon.

Distal end 34 of the outer sheath 14 may be configured with a tapered portion 40 that extends towards a center axis A-A of the outer sheath 14 to a distal edge 42 that surrounds an opening in the distal end 34 of the outer sheath 14. Tapered portion 40 serves to ease the transition between the outer sheath 14 and a distal tip portion 40, without drag, trauma or coring of tissue from a diameter that defines the body portion 24 of the introducer 12 to a diameter that defines the body portion 38 of the outer sheath 14. In one exemplary configuration, distal end 34 may be configured with a radius or other configuration so as to create a smooth/atraumatic transition of the brain tissue when surgical access assembly 10 is inserted into the brain.

Figure 4:
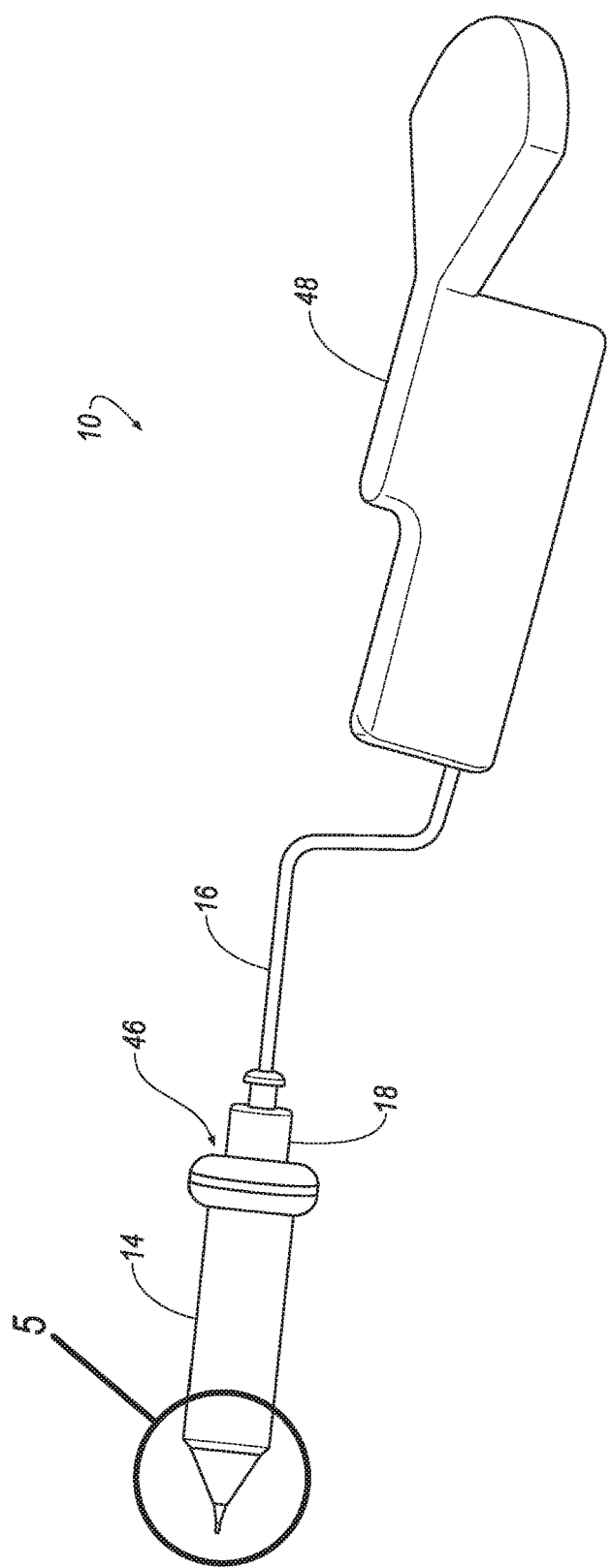
FIG. 4 is a perspective view a surgical access system with an alternative arrangement of the introducer element disposed in the outer sheath and the navigational stylet positioned within the introducer element.

Referring to FIGS. 3A and 3B, the navigational stylet 16 includes a distal tip 32 and an elongated body portion. The elongated body portion has a proximal end 46 operatively connected to a navigational element 48, as shown in FIG. 4. In one exemplary arrangement, the elongated body portion of the stylet 16 is offset such that the navigational element 48 is out of the line of site of the operator during insertion of the surgical access system. The navigational stylet 16 is removably positioned within the channel 50 formed through the introducer 12. As discussed above, in one exemplary arrangement, the channel 50 is narrow so as only to be slightly larger than the diameter of the navigational stylet 16. With this arrangement, the relative position of the stylet 16 within in the introducer is maintained as the channel 50 may serve as an alignment feature for the stylet 16 with respect to the distal tip 31 of the introducer. In the exemplary configuration shown in FIGS. 3A and 3B, the distal tip 32 of the navigational stylet 16 may be seated adjacent a distal tip 31 of the introducer 12. More specifically, the channel 50 may terminate with an inwardly directing seat, which is complementary to the taper configuration of the distal tip 32 to insure proper placement of the navigational stylet 16 within the introducer 12. As discussed above, the predetermined offset from the distal tip 31 of the introducer and the distal tip 32 of the navigational stylet 16 may be programmed into a navigational system to allow the user to know where the distal tip of introducer 12 is during movement of the surgical access system to an area of interest in the patient. In the embodiment of FIGS. 4 and 5, the distal tip 32 of the navigational stylet 16 is configured to extend through the opening 30 of the introducer 12 so as to protrude through the opening 30.

In use, the navigational stylet 16 is inserted into the channel 50 of the introducer 12. In one exemplary arrangement, the navigational stylet 16 may be provided with depth markers (not shown) on the outside surface. The depth markers serve as a reference to a user to indicate how far the navigational stylet is inserted into the introducer and subsequently how far the stylet protrudes from the introducer, for the arrangement shown in FIG. 5. In use, the operator cannot see the distal tip of the introducer. Thus, having a reference point is very beneficial. To maintain the navigational stylet 16 in position, thereby not requiring a user to hold the navigational stylet 16 in position during the introduction of the surgical access assembly 10 to an area of interest, in one exemplary arrangement, a locking member 18 may be provided to lock the introducer 12 to the navigational stylet 16. In one exemplary arrangement, a touhy-borst connector may serve as the locking member 18. The touhy-borst connector will also serve as a depth stop to prevent damage to the distal tip 32 of the navigational stylet 16.

In an alternative arrangement, the introducer 12 may further comprise an opening (not shown) positioned adjacent the proximal end 22 of the introducer 12 or through the handle portion 26. A set screw (not shown) may be directed through the opening to contact the navigational stylet 16 and retain the navigational stylet 16 to the introducer 12, as disclosed in copending U.S. application Ser. No. 13/444,732.

Once the navigational stylet 16 is selectively attached to the introducer 12, the outer sheath 14 is positioned over the introducer 12 until the tapered tip member 28 extends distally from the tapered portion 40 of the outer sheath 14. Once the outer sheath 14 is positioned on the introducer 12, the surgical access system 10 may be directed into brain tissue to a location of interest. Due to the configuration of the distal tips 31/32, brain tissue is atraumatically pushed away from the surgical access system 10, without causing undue damage to the tissue.

Once the navigational stylet 16 indicates that the location of interest has been reached, the introducer 12 may then be removed from the outer sheath 14, while leaving the outer sheath 14 in place. The outer sheath 14 will then serve as an access pathway to an area of interest.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A surgical access system, comprising: an outer sheath defined by an open distal end and an open proximal end and including a hollow body portion therebetween; an introducer defined by a distal end and a proximal end, wherein the distal end further comprises a tapered distal tip member that terminates in a distal tip, wherein the introducer further comprises a channel disposed through the introducer and the channel terminates in an inwardly tapered distal end spaced proximally from the distal tip; and a navigational stylet selectively positioned within the inwardly tapered distal end of the channel so as to receive the distal end of the navigational element therein spaced from the distal tip of the introducer, when the navigational element is in an introducing configuration; wherein the navigational stylet is configured to indicate a location of the introducer within a patient during use; wherein the introducer is configured to be received within the outer sheath such that the tapered distal tip member protrudes from the open distal end of the outer sheath when the introducer is in the introducing configuration.

2. The surgical access system of claim 1, wherein the distal end of the introducer has a conical shape.

3. The surgical access system of claim 1, wherein the navigational stylet further comprises depth markers.

4. The surgical access system of claim 1, further comprising a locking member configured to retain the introducer to the navigational element stylet while in the introduction configuration.

5. The surgical access system of claim 4, wherein the locking member is a touhy-borst connector.

6. The surgical access system of claim 1, wherein the channel is centered within the introducer so as to center the navigational stylet within the introducer.

7. The surgical access system of claim 1, wherein the navigational stylet has a body portion with an offset such that the navigational element is offset from the introducer when the stylet is positioned within the channel.

8. The surgical access system of claim 1, wherein the outer sheath further includes a tapered section positioned at the distal end of the outer sheath.

* * * * *